United States Patent
Leung et al.

(10) Patent No.: US 12,227,538 B2
(45) Date of Patent: Feb. 18, 2025

(54) GLUCOCORTICOID RECEPTOR AGONISTS

(71) Applicant: Eli Lilly and Company, Indianapolis, IN (US)

(72) Inventors: Donmienne Doen Mun Leung, San Diego, CA (US); Jacqueline Mary Wurst, Indianapolis, IN (US); James Andrew Jamison, La Jolla, CA (US)

(73) Assignee: Eli Lilly and Company, Indianapolis, IN (US)

( * ) Notice: Subject to any disclaimer, the term of this patent is extended or adjusted under 35 U.S.C. 154(b) by 421 days.

(21) Appl. No.: 17/700,910

(22) Filed: Mar. 22, 2022

(65) Prior Publication Data

US 2022/0306680 A1    Sep. 29, 2022

Related U.S. Application Data

(60) Provisional application No. 63/164,603, filed on Mar. 23, 2021.

(51) Int. Cl.
*C07J 17/00* (2006.01)
*A61P 17/00* (2006.01)

(52) U.S. Cl.
CPC ............. *C07J 17/00* (2013.01); *A61P 17/00* (2018.01); *C07J 17/005* (2013.01)

(58) Field of Classification Search
CPC ........... C07J 17/00; C07J 17/005; A61P 17/00
See application file for complete search history.

(56) References Cited

U.S. PATENT DOCUMENTS 8,524,697 B2    9/2013    Anthes et al.

FOREIGN PATENT DOCUMENTS

| WO | WO-02080931 A1 * | 10/2002 | ....... A61K 47/48023 |
|---|---|---|---|
| WO | 2006/138212 A1 | 12/2006 | |
| WO | 2009/069032 A2 | 6/2009 | |
| WO | 2009/085879 A2 | 7/2009 | |
| WO | 2009/108118 A1 | 9/2009 | |
| WO | 2017/132103 A2 | 8/2017 | |
| WO | 2017/210471 A1 | 12/2017 | |
| WO | 2018/089373 A9 | 5/2018 | |
| WO | 2019/106608 A1 | 6/2019 | |
| WO | 2019/106609 A1 | 6/2019 | |
| WO | 2021/216913 A1 | 10/2021 | |

OTHER PUBLICATIONS

Elewaut et al. Targeting inflammation using selective glucocorticoid receptor modulators, Curr. Opin. Pharmacol. 2010, 10:497-504 (Year: 2010).*
Law et al. The Role of Autophagy in Lupus Nephritis, Int. J. Mol. Sci. 2015, 16:25154-25167 (Year: 2015).*
Millan, D.S. et al., "Design and Synthesis of Long Acting Inhaled Corticosteroids for the Treatment of Asthma," Bioorganic & Medicinal Chemistry Letters, 2011, pp. 5826-5830, vol. 21.

* cited by examiner

*Primary Examiner* — Layla D Berry
*Assistant Examiner* — Sarah Grace Scrivener
(74) *Attorney, Agent, or Firm* — Gabriel Magallanes

(57) ABSTRACT

Provided herein are compounds that are glucocorticoid receptor agonists useful for the treatment of autoimmune and inflammatory diseases, processes for preparing these compounds, and pharmaceutical compositions comprising these compounds.

23 Claims, No Drawings

GLUCOCORTICOID RECEPTOR AGONISTS

The present disclosure provides compounds that are glucocorticoid receptor agonists and are useful for the treatment of autoimmune and inflammatory diseases, such as atopic dermatitis, inflammatory bowel disease, systemic lupus erythematosus, lupus nephritis, and rheumatoid arthritis, processes for preparing these compounds, pharmaceutical compositions comprising these compounds, and methods of using these compounds and compositions are also provided.

Atopic dermatitis is a chronic, pruritic relapsing and remitting inflammatory skin disease that occurs frequently in children, but also affects many adults. Current treatments of atopic dermatitis include light therapy, topical creams containing corticosteroids or calcineurin inhibitors, or a subcutaneous injectable biologic known as dupilumab. In spite of progress made in treating atopic dermatitis, there remains a significant need for new compounds to treat atopic dermatitis and other inflammatory and autoimmune diseases WO2017/210471 discloses certain glucocorticoid receptor agonists and immunoconjugates thereof useful for treating autoimmune or inflammatory diseases. WO2018/089373 discloses novel steroids, protein conjugates thereof, and methods for treating diseases, disorders, and conditions comprising administering the steroids and conjugates.

The present invention provides certain novel compounds which are glucocorticoid receptor agonists. The present invention further provides certain novel compounds which are prodrugs of glucocorticoid receptor agonists. In addition, the present invention provides certain novel compounds which are glucocorticoid receptor agonists useful in the treatment of autoimmune and inflammatory diseases such as atopic dermatitis, inflammatory bowel disease, rheumatoid arthritis, systemic lupus erythematosus, and lupus nephritis.

Accordingly, in one embodiment, the invention provides a compound of Formula I:

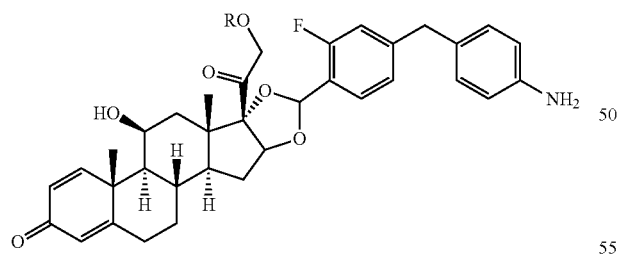

Formula I wherein R is hydrogen, —P(=O)(OH)$_2$,

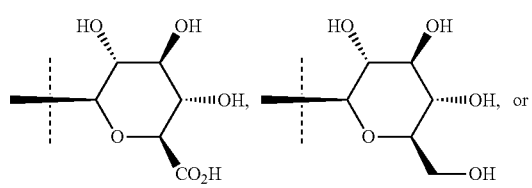

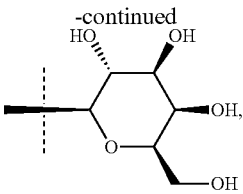

or a pharmaceutically acceptable salt thereof.

In an embodiment, R is hydrogen.
In an embodiment, R is —P(=O)(OH)$_2$.
In an embodiment, R is:

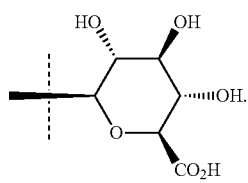

In an embodiment, R is:

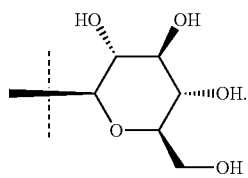

In an embodiment, R is:

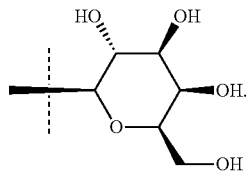

In a particular embodiment, the invention provides a compound of Formula Ia:

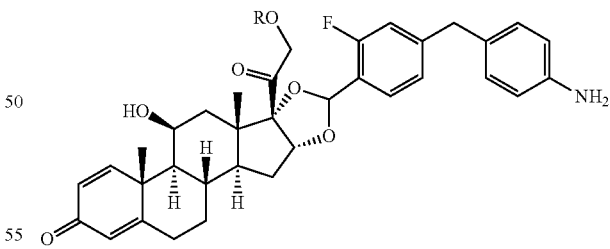

Formula Ia wherein R is hydrogen, —P(=O)(OH)$_2$,

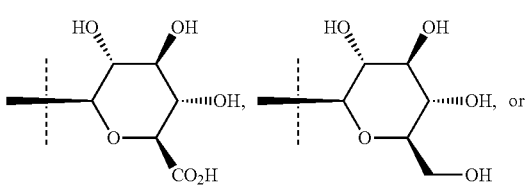

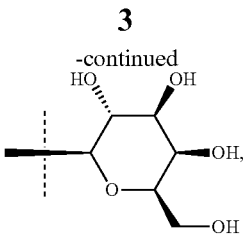

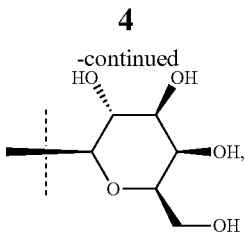

or a pharmaceutically acceptable salt thereof.

In a particular embodiment, the invention provides a compound of Formula Ib:

Formula Ib

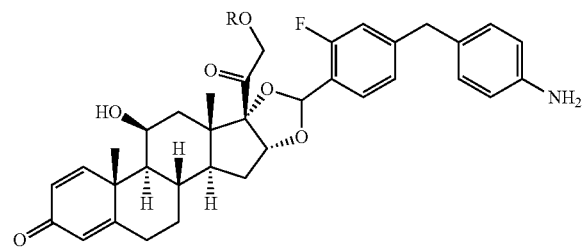

wherein R is hydrogen, —P(=O)(OH)$_2$,

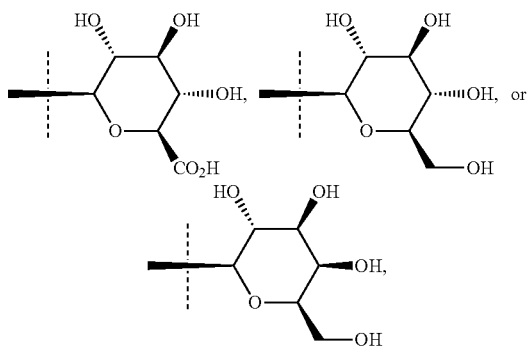

or a pharmaceutically acceptable salt thereof.

In a particular embodiment, the invention provides a compound of Formula Ic:

Formula Ic

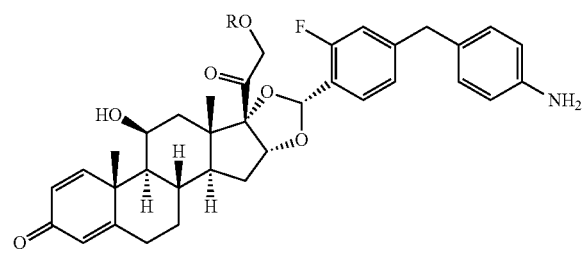

wherein R is hydrogen, —P(=O)(OH)$_2$,

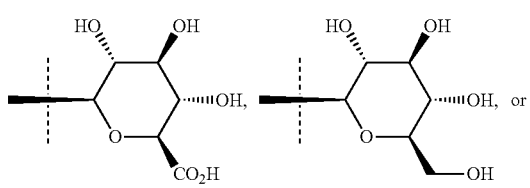

or a pharmaceutically acceptable salt thereof.

In an embodiment, the present invention also provides a method of treating an inflammatory disease in a patient in need of such treatment, comprising administering to the patient an effective amount of a compound of Formula I, or a pharmaceutically acceptable salt thereof. In an embodiment, the present invention also provides a method of treating atopic dermatitis in a patient in need of such treatment, comprising administering to the patient an effective amount of a compound of Formula I, or a pharmaceutically acceptable salt thereof. In an embodiment, the present invention further provides a method of treating inflammatory bowel disease in a patient in need of such treatment, comprising administering to the patient an effective amount of a compound of Formula I, or a pharmaceutically acceptable salt thereof. In an embodiment, the present invention further provides a method of treating rheumatoid arthritis in a patient in need of such treatment, comprising administering to the patient an effective amount of a compound of Formula I, or a pharmaceutically acceptable salt thereof. In an embodiment, the present invention also provides a method of treating systemic lupus erythematosus in a patient in need of such treatment, comprising administering to the patient an effective amount of a compound of Formula I, or a pharmaceutically acceptable salt thereof. In an embodiment, the present invention also provides a method of treating lupus nephritis in a patient in need of such treatment, comprising administering to the patient an effective amount of a compound of Formula I, or a pharmaceutically acceptable salt thereof.

In an embodiment, the present invention further provides a compound of Formula I, or a pharmaceutically acceptable salt thereof for use in therapy. In an embodiment, the present invention provides a compound of Formula I, or a pharmaceutically acceptable salt thereof for use in treating an inflammatory disease. In an embodiment, the present invention provides a compound of Formula I, or a pharmaceutically acceptable salt thereof, for use in treating atopic dermatitis. In an embodiment, the present invention provides a compound of Formula I, or a pharmaceutically acceptable salt thereof, for use in treating rheumatoid arthritis. In an embodiment, the present invention provides a compound of Formula I, or a pharmaceutically acceptable salt thereof, for use in treating inflammatory bowel disease. In an embodiment, the present invention provides a compound of Formula I, or a pharmaceutically acceptable salt thereof, for use in treating lupus nephritis. In an embodiment, the present invention provides a compound of Formula I, or a pharmaceutically acceptable salt thereof, for use in treating systemic lupus erythematosus.

In an embodiment, the present invention also provides the use of a compound of Formula I, or a pharmaceutically acceptable salt thereof, for the manufacture of a medicament for treating an inflammatory disease. In an embodiment, the present invention provides the use of a compound of Formula I, or a pharmaceutically acceptable salt thereof, for the manufacture of a medicament for treating atopic dermatitis. In an embodiment, the present invention provides the use of a compound of Formula I, or a pharmaceutically acceptable salt thereof, for the manufacture of a medicament for treating rheumatoid arthritis. In an embodiment, the present invention further provides the use of a compound of Formula I, or a pharmaceutically acceptable salt thereof, for the manufacture of a medicament for treating inflammatory bowel disease. In an embodiment, the present invention further provides the use of a compound of Formula I, or a pharmaceutically acceptable salt thereof, for the manufacture of a medicament for treating lupus nephritis. In an embodiment, the present invention also provides the use of a compound of Formula I, or a pharmaceutically acceptable salt thereof, for the manufacture of a medicament for treating systemic lupus erythematosus.

In an embodiment, the present invention further provides a pharmaceutical composition, comprising a compound of Formula I, or a pharmaceutically acceptable salt thereof, with one or more pharmaceutically acceptable carriers, diluents, or excipients. In an embodiment, the present invention further provides a process for preparing a pharmaceutical composition, comprising admixing a compound of Formula I, or a pharmaceutically acceptable salt thereof, with one or more pharmaceutically acceptable carriers, diluents, or excipients. In an embodiment, the present invention also encompasses novel intermediates and processes for the synthesis of compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, it is understood that Formula I encompasses Formulas Ia, Ib, and Ic, and all references to Formula I herein should be read as including Formulas Ia, Ib, and Ic.

The compounds of the present invention can be formulated as pharmaceutical compositions administered by any route which makes the compound bioavailable including topical administration. In addition, compounds of the present invention can be formulated as antibody drug conjugates (ADC) wherein certain compounds of Formula I are recognized by one of skill in the art as the payload portion of the ADC. Such ADCs are administered by injection, particularly subcutaneous injection. Furthermore, compounds of the present invention that have the hydroxy group at C21 capped wherein R is —P(═O)(OH)$_2$,

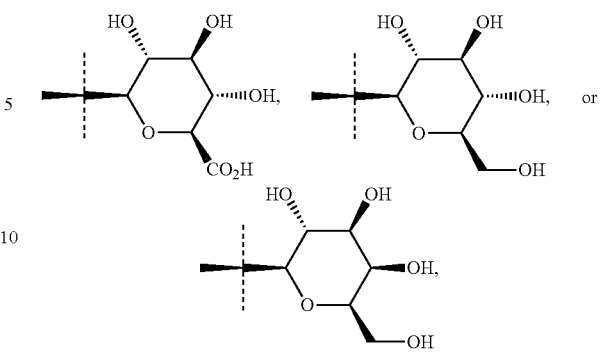

behave as prodrugs and are metabolized in vitro or in vivo to provide the active glucocorticoid receptor agonist wherein R is hydrogen. Such pharmaceutical compositions, ADCs, and processes for preparing same are well known in the art (See, e.g., Remington: The Science and Practice of Pharmacy, L. V. Allen, Editor, 22$^{nd}$ Edition, Pharmaceutical Press, 2012; WO 2017/062271, and WO 2017/210471).

Included within the scope of the present invention is a pharmaceutically acceptable salt of Formula I. A pharmaceutically acceptable salt of a compound of the invention, such as a compound of Formula I can be formed, for example, by reaction of an appropriate free base of a compound of the invention with an appropriate pharmaceutically acceptable acid in a suitable solvent such as diethyl ether under standard conditions well known in the art. See, for example, Berge, S. M., et al., "Pharmaceutical Salts," *Journal of Pharmaceutical Sciences*, 66: 1-19, (1977).

Certain abbreviations are defined as follows: "DMSO" refers to dimethyl sulfoxide; "DCM" refers to methylene chloride or dichloromethane; "g" refers to gram or grams; "rt" refers to room temperature; "g" refers to grams; "hr" or "hrs" refers to hour or hours; "mg" refers to milligrams; "min" refers to minute or minutes; "mL" refers to milliliter or milliliters; "mol" refers to mole or moles; "mmol" refers to millimole or millimoles; "nm" refers to nanometer or nanometers; "ES/MS" refers to Electrospray Mass Spectrometry; and "m/z" refers to mass-to-charge ration for mass spectroscopy.

The compounds of the present invention, or salts thereof, may be readily prepared by a variety of procedures known to one of ordinary skill in the art, some of which are illustrated in the preparations and examples below. One of ordinary skill in the art recognizes that the specific synthetic steps for each of the routes described may be combined in different ways, or in conjunction with steps from different schemes, to prepare compounds of the invention, or salts thereof. The product of each step can be recovered by conventional methods well known in the art, including extraction, evaporation, precipitation, chromatography, filtration, trituration, and crystallization. All substituents unless otherwise indicated, are as previously defined. The reagents and starting materials are readily available to one of ordinary skill in the art. The following preparations, examples, and assays further illustrate the invention, but should not be construed to limit the scope of the invention in any way.

PREPARATION 1 tert-Butyl N-[4-[(3-fluoro-4-formyl-phenyl)methyl]phenyl]carbamate

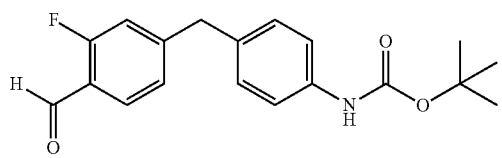 [SMILES: CC(C)(C)OC(=O)Nc1ccc(Cc2ccc(C=O)c(F)c2)cc1]

tert-Butyl (4-(bromomethyl) phenyl)carbamate (3.4 g, 11.6 mmol), 2-fluoro-4-(4,4,5,5-tetramethyl-1,3,2-dioxaborolan-2-yl)benzaldehdye (1.9 g, 7.7 mmol) and potassium carbonate (39 g, 285 mmol) were dissolved in toluene (50 mL, 470 mmol) and water (10 mL, 560 mmol). The solution was degassed pulling vacuum and backfilling with nitrogen three times. 1,1'-Bis(diphenylphosphino)ferrocene palladium(II)dichloride dichloromethane complex (0.977 g, 1.2 mmol) was added, and the reaction was heated to reflux for 18 hrs. After the reaction was cooled back to rt, water (100 mL) and ethyl acetate (150 mL) were added. The layers were separated, organic layer was dried over magnesium sulfate, filtered, and concentrated under reduced pressure. The residue was purified by normal phase purification (silica gel), eluting with 4:1 heptanes:ethyl acetate to give the title compound (1.36 g, 53% yield). ES/MS m/z 328.2 (M−H).

PREPARATION 2

(2R,3S,4S,5R,6R)-2-(Acetoxymethyl)-6-(2-((6aR,6bS,7S,8aS,8bS,10R,11aR,12aS,12bS)-10-(4-(4-aminobenzyl)-2-fluorophenyl)-7-hydroxy-6a,8β-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)tetrahydro-2H-pyran-3,4,5-triyl triacetate

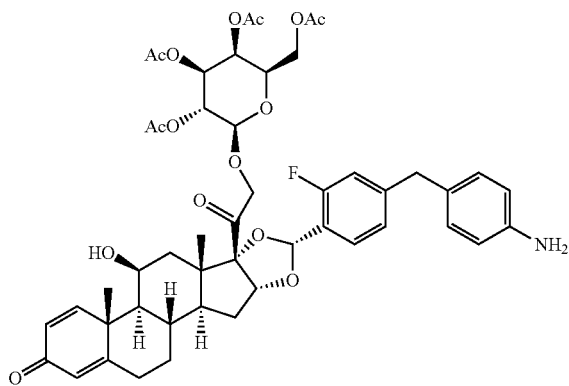

Molecular sieves (3 Å, 0.5 g), (6aR,6bS,7S,8aS,8bS,10R,11aR,12aS,12bS)-10-(4-(4-aminobenzyl)-2-fluorophenyl)-7-hydroxy-8b-(2-hydroxyacetyl)-6a,8β-dimethyl-1,2,6a,6b,7,8,8a,8b,11a,12,12a,12b-dodecahydro-4H-naphtho[2',1':4,5]indeno[1,2-d][1,3]dioxol-4-one (isomer 1) (200 mg, 0.34 mmol, see Example 1), and 2,3,4,6-tetra-O-acetyl-alpha-D-galactopyranosyl bromide (175 mg, 0.43 mmol) were dissolved in dichloromethane (7 mL, 109 mmol) and stirred at rt for 1 hr. The reaction was cooled to 0° C. and silver (I) oxide (160 mg, 0.68 mmol) was added in one portion, and then trimethylsilyl trifluoromethanesulfonate (65 µL, 0.35 mmol) was added dropwise over 3 min while stirring the reaction vigorously for 30 min. The crude reaction was diluted with 20 mL dichloromethane and 2 mL water was added. The solution was filtered over diatomaceous earth and washed with dichloromethane, ethyl acetate, and methanol. The crude solution was concentrated under reduced pressure to give a residue. The residue was purified by reverse phase chromatography, eluting with 1:9 10 mM ammonium bicarbonate water +5% methanol:acetonitrile to give the title compound (85 mg, 27% yield). ES/MS m/z 918.4 (M).

PREPARATION 3

(2R,3R,4S,5S,6S)-2-(2-((6aR,6bS,7S,8aS,8bS,10R,11aR,12aS,12bS)-10-(4-(4-Aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)-6-(methoxycarbonyl)tetrahydro-2H-pyran-3,4,5-triyl triacetate

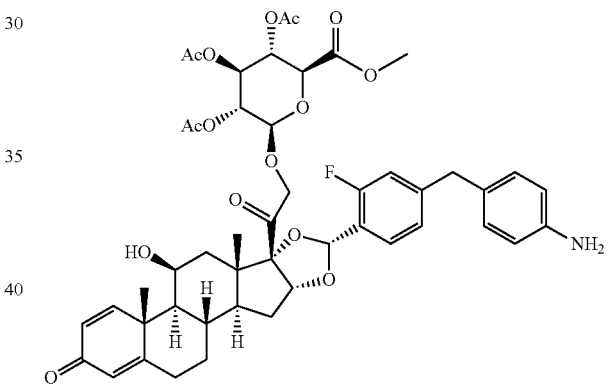

Molecular sieves (3 Å, 0.5 g), (6aR,6bS,7S,8aS,8bS,10R,11aR,12aS,12bS)-10-(4-(4-aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (isomer 1) (200 mg, 0.34 mmol, see Example 1), and 2,3,4,6-tetra-acetobromo-alpha-D-glucoronic acid methyl ester (182 mg, 0.43 mmol) were dissolved in dichloromethane (7 mL, 109 mmol) and stirred at rt for 1 hr. The reaction was cooled to 0° C. and silver (I) oxide (160 mg, 0.68 mmol) was added in one portion, and then trimethylsilyl trifluoromethanesulfonate (65 µL, 0.35 mmol) was added in one portion. The reaction was stirred at 0° C. for 40 min and then warmed to rt for 10 min. The crude reaction was diluted with 15 mL dichloromethane and 2 mL water was added. The solution was filtered over diatomaceous earth and washed with dichloromethane, ethyl acetate, and methanol. The crude solution was concentrated under reduced pressure to give a residue. The residue was purified by reverse phase chromatography, eluting with 1:9 10 mM ammonium bicarbonate water+5% methanol:acetonitrile to give the title compound (44 mg, 14% yield). ES/MS m/z 904.4 (M+H).

PREPARATION 4

9H-Fluoren-9-ylmethyl N-[4-[(3-fluoro-4-formyl-phenyl)methyl]phenyl]carbamate

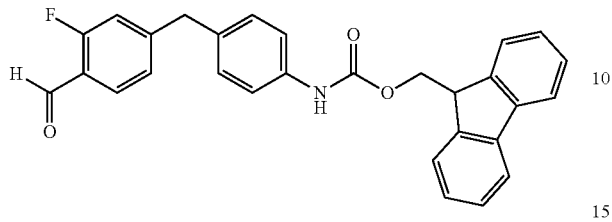

To a solution of tert-butyl N-[4-[(3-fluoro-4-formyl-phenyl)methyl]phenyl]carbamate (3.7 mg, 13 mmol, see Preparation 1) in acetonitrile (40 mL) and water (10 mL) at 0° C. was added sodium bicarbonate (1.9 g, 23 mmol) and 9-fluorenylmethyl chloroformate (3.3 g, 12 mmol) in one portion. The reaction was warmed to 15° C. after the addition and stirred for 12 hrs. The crude solution was concentrated under reduced pressure to give a residue. The residue was resuspended in water (50 mL) and extracted with ethyl acetate (50 mL×3). The combined organic layers were washed with brine (40 mL), dried over sodium sulfate, filtered, and concentrated under reduced pressure. The residue was purified by normal phase chromatography (silica gel), eluting with 9:1 petroleum ether:ethyl acetate to give the title compound (1.6 g, 24% yield). ES/MS m/z 452.4 (M+H).

PREPARATION 5

(9H-Fluoren-9-yl)methyl (4-(3-fluoro-4-((6aR,6bS, 7S,8aS,8bS,10R, 11aR,12aS,12bS)-7-hydroxy-8b-(2-hydroxyacetyl)-6a,8a-dimethyl-4-oxo-2,4,6a,6b,7, 8,8a, 8b,11a,12,12a,12b-dodecahydro-1H-naphtho [2',1':4,5]indeno[1,2-d][1,3]dioxol-10-yl)benzyl) phenyl)carbamate

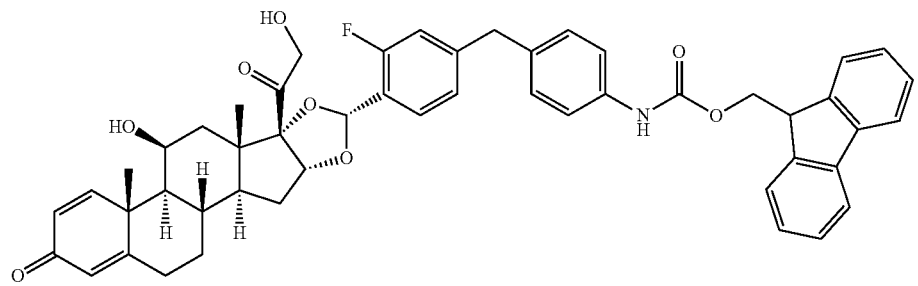

To a solution of 9H-fluoren-9-ylmethyl N-[4-[(3-fluoro-4-formyl-phenyl)methyl]phenyl]carbamate (1.5 g, 2.9 mmol, see Preparation 4) and (8S,9S,10R,11S,13S,14S,16R, 17S)-11,16,17-trihydroxy-17-(2-hydroxyacetyl)-10,13-dimethyl-7,8,9,11,12,14,15,16-octahydro-6H-cyclopenta[a] phenanthren-3-one (1.3 g, 3.5 mmol) in acetonitrile (15 mL, 290 mmol) at 0° C. was added perchloric acid (70% in water, 1.3 mL, 17 mmol) dropwise. The reaction was stirred at 0° C. for 30 min and warmed to rt over 6 h. The reaction was poured over 30 mL saturated aqueous sodium bicarbonate. The crude solution was concentrated under reduced pressure to give a residue. The residue was taken up in ethyl acetate (50 mL) and water (30 mL) and was extracted with ethyl acetate (50 mL×2). The combined organic layers were washed with brine (50 mL), dried over sodium sulfate, filtered, and concentrated under reduced pressure. The residue was purified by normal phase chromatography (silica gel), eluting with 9:1 dichloromethane:methanol to give the title compound (1.5 g, 61% yield). ES/MS m/z 810.3 (M+H).

PREPARATION 6

(9H-Fluoren-9-yl)methyl (4-(4-((6aR,6bS,7S,8aS, 8bS,10R,11aR,12aS,12bS)-8b-(2-((di-tert-butoxy-phosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)-3-fluorobenzyl)phenyl)carbamate

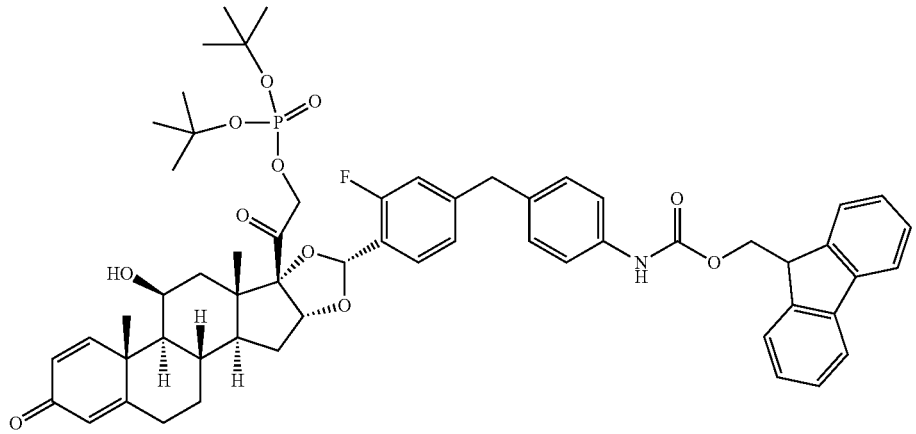

1H-Tetrazole (520 mg, 7.3 mmol) and N-ditert-butoxy-phosphanyl-N-ethyl-ethanamine (1.9 g, 7.1 mmol), in one portion, were added to a solution of (9H-fluoren-9-yl)methyl (4-(3-fluoro-4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)carbamate (650 mg, 0.75 mmol, see Preparation 5) in dimethylformamide (7 mL, 90 mmol) at rt, under nitrogen atmosphere. After 3 hrs, the reaction was cooled to 0° C. and hydrogen peroxide (1.9 g, 7.5 mmol) was added and the reaction was warmed back to room temperature over 4 hrs. The reaction was quenched by the addition of sodium thiosulfate (10 mL), poured over water (15 mL), and extracted with ethyl acetate (25 mL) three times. The combined organic layers were washed with brine (50 mL), dried over sodium sulfate, and concentrated under reduced pressure to give a residue. The residue was purified by normal phase chromatography (silica gel), eluting with 1:1 petroleum ether:ethyl acetate to give the title compound (250 mg, 33% yield). ES/MS m/z 1002.3 (M+H).

PREPARATION 7

2-((6aR,6bS,7S,8aS,8bS,10R,11aR,12aS,12bS)-10-(4-(4-Aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl di-tert-butyl phosphate

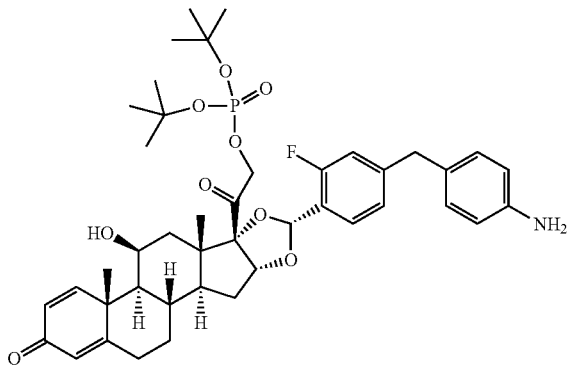

(9H-Fluoren-9-yl)methyl (4-(4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)-3-fluorobenzyl)phenyl)carbamate (250 mg, 0.25 mmol, see Preparation 6) was dissolved in acetonitrile (4 mL, 76 mmol) and piperidine (200 μL, 2.0 mmol) was added. The reaction was stirred at rt for 20 min. The crude solution was concentrated under reduced pressure to give a residue. The residue was taken up in 10 mL petroleum ether and stirred for 2 hrs. The resulting solid was collected by filtration and dried under reduced pressure to give the title compound (165 mg, 77% yield). ES/MS m/z 780.3 (M+H).

PREPARATION 8

(2R,3R,4S,5R,6R)-2-(Acetoxymethyl)-6-(2-((6aR,6bS,7S,8aS,8bS,10R,11aR,12aS,12bS)-10-(4-(4-aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)tetrahydro-2H-pyran-3,4,5-triyl triacetate

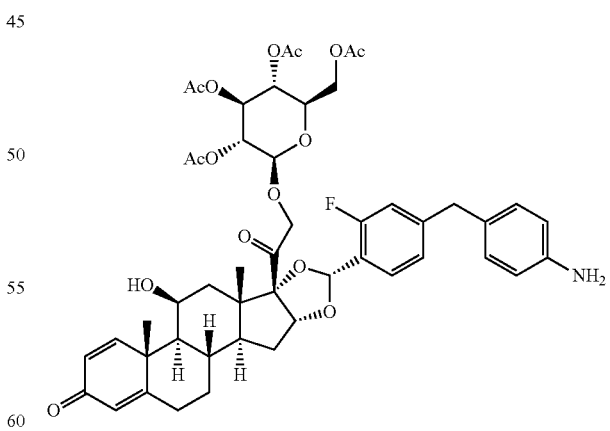

Molecular sieves (3 Å, 0.5 g), (6aR,6bS,7S,8aS,8bS,10R,11aR,12aS,12bS)-10-(4-(4-Aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (isomer 1) (300 mg, 0.51 mmol, see Example 1), and 2,3,4,6-tetra-O-acetyl-alpha-D- glucopyranosyl bromide (320 mg, 0.77 mmol), were dissolved in dichloromethane (7 mL) and stirred at rt for 1 h. The reaction was cooled to 0° C. Silver (I) oxide (240 mg, 1.0 mmol) and trimethylsilyl trifluoromethanesulfonate (100 µL, 0.54 mmol) were added. After 30 min, the reaction was quenched with saturated aqueous sodium bicarbonate, filtered over celite, and was rinsed with DCM (10 mL) and MeOH (10 mL). The combined organic layers were concentrated under reduced pressure to give a residue. The residue was purified by reverse phase chromatography, eluting with 1:2 10 mM ammonium bicarbonate water +5% methanol:acetonitrile to give the title compound (120 mg, 26% yield). MS m/z 918.4 (M).

Example 1

(6aR,6bS,7S,8aS,8bS,10R,11aR,12aS,12bS)-10-(4-(4-Aminobenzyl)-2-fluorophenyl)-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5] indeno[1,2-d][1,3]dioxol-4-one (isomer 1)

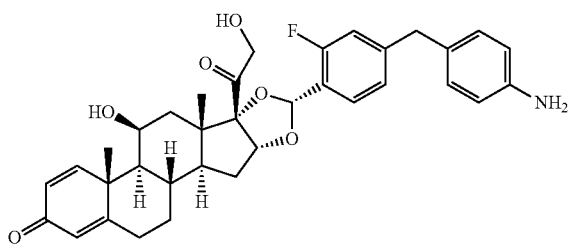

Perchloric acid (70% in water, 3 mL) was added to (8S,9S,10R,11S,13S,14S,16R,17S)-11,16,17-trihydroxy-17-(2-hydroxyacetyl)-10,13-dimethyl-7,8,9,11,12,14,15,16-octahydro-6H-cyclopenta[a]phenanthrene-3-one (2.5 g, 6.6 mmol) and tert-butyl N-[4-[(3-fluoro-4-formyl-phenyl)methyl]phenyl]carbamate (2.2 g, 6.7 mmol, see Preparation 1) in acetonitrile (50 mL) at rt and stirred. After 18 hours, the reaction was quenched with saturated aqueous sodium bicarbonate and was extracted with 9:1 methylene chloride:isopropanol. The organic layers were combined, dried over magnesium sulfate, filtered, and concentrated under reduced pressure to give a residue. The residue was purified by reverse phase chromatography, eluting with 1:1 10 mM ammonium bicarbonate water +5% methanol:acetonitrile to give the title compound, isomer 1, peak 1 (2.25 g, 58% yield). ES/MS m/z 588.4 (M+H). $^1$H NMR (500.11 MHz, d$_6$-DMSO) δ 0.86 (s, 3H); 1.06-1.01 (m, 2H), 1.39 (s, 3H), 1.80-1.73 (m, 5H), 2.16-2.13 (m, 2H), 2.38-2.28 (m, 1H), 2.59-2.53 (m, 1H), 3.74 (s, 2H), 4.20-4.15 (m, 1H), 4.30-4.29 (m, 1H), 4.50-4.45 (m, 1H), 4.94-4.79 (m, 4H), 5.12 (t, J=6.0 Hz, 1H), 5.59 (s, 1H), 5.93 (s, 1H), 6.16 (dd, J=1.8, 10.1 Hz, 1H), 6.49-6.46 (m, 2H), 6.86 (d, J=8.3 Hz, 2H), 7.06-7.00 (m, 2H), 7.32-7.30 (m, 1H), 7.46 (t, J=7.7 Hz, 1H)

Example 1 (Additional Preparation)

(6aR,6bS,7S,8aS,8bS,10R,11aR,12aS,12bS)-10-(4-(4-Aminobenzyl)-2-fluorophenyl)-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5] indeno[1,2-d][1,3]dioxol-4-one Perchloric acid (70% w/w in water, 12 mL, 140 mmol, 3.5 equiv) was added dropwise to a cold (0-3° C.) slurry of a mixture of (8S,9S,10R,11S,13S,14S,16R,17S)-11,16,17-trihydroxy-17-(2-hydroxyacetyl)-10,13-dimethyl-7,8,9,11,12,14,15,16-octahydro-6H-cyclopenta[a]phenanthrene-3-one (15.00 g, 39.85 mmol) and tert-butyl N-[4-[(3-fluoro-4-formyl-phenyl)methyl]phenyl]carbamate (13.12 g, 39.85 mmol, see Preparation 1) in acetonitrile (750 mL, 589 g, 50 volumes, 360 equiv, 14.34 mol). After 10 min the cooling bath was removed, and the mixture was stirred at ambient temperature for 18 hrs. Solid NaHCO$_3$ (16.8 g, 200 mmol) was added portion wise, and the pH was adjusted to neutral. After stirring for 1 hr the mixture was filtered and washed with 50 mL of acetonitrile. The clear solution was then treated with a solution of ®-anicyphos (10.84 g, 39.85 mmol) in methanol (325 mL) in one portion and with approximately 5 mg of the salt. The mixture was stirred at ambient temperature for 16 hrs, and the resulting suspension was filtered, washed with acetonitrile (3×50 mL) and dried under vacuum at 45° C. to afford 17.8 g of (6aR,6bS,7S,8aS,8bS,10R,11aR,12aS,12bS)-10-(4-(4-aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one-(R)-anicyphos salt as a white solid (52% yield). HPLC-MS of the solid showed (corrected for anicyphos peak at 0.68) at 215/242 nm: 1.69 min; 95.5/96 area % a/a (desired isomer); 1.75 min; 1.3/1.4 area % a/a (undesired isomer).

A mixture of (6aR,6bS,7S,8aS,8bS,10R,11aR,12aS,12bS)-10-(4-(4-aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one-(R)-anicyphos salt (20 g, 23 mmol) with 200 mL DCM and 200 mL saturated aqueous NaHCO$_3$ was vigorously stirred until all solid were dissolved (typically overnight). The layers were then separated, and the aqueous layer was extracted with 2×50 mL of DCM. The combined organic phase was washed with 2×50 mL of saturated NaCl, dried over anhydrous Na$_2$SO$_4$, and was concentrated under vacuum at 45° C. to give 12.5 g of the title compound as a white solid (91% yield). HPLC purity: 96.6% at 215 nm; 96.9% at 242 nm. ES/MS m/z 588.2 (M+1). Q-NMR (9.5 mg product+3.0 mg TCNB (MW 260.89). Purity 90% w/w. Residual DCM 1% w/w. $^1$H NMR (500.11 MHz, CDCl$_3$) δ 0.95 (s, 3H); 1.20-1.03 (m, 2H), 1.44-1.37 (m, 4H), 1.84-1.56 (m, 3H), 1.97-1.90 (m, 1H), 2.25-2.00 (m, 3H), 2.38-2.29 (m, 1H), 2.62-2.50 (m, 1H), 3.08-2.90 (m, 1H), 3.68-3.47 (m, 1H), 3.82 (s, 2H), 4.32-4.23 (d, 1H), 4.49 (m, 1H), 4.65-4.58 (d, 1H), 5.08-5.03 (d, 1H), 5.63 (s, 1H), 6.00 (s, 1H), 6.27-6.23 (d, J=8.3 Hz, 1H), 6.60 (d, J=8.3 Hz, 2H), 6.99-6.82 (m, 3H), 7.23-7.16 (m, 1H), 7.35 (t, J=7.7 Hz, 1H).

Example 2

(6aR,6bS,7S,8aS,8bS,10S,11aR,12aS,12bS)-10-(4-(4-Aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (isomer 2)

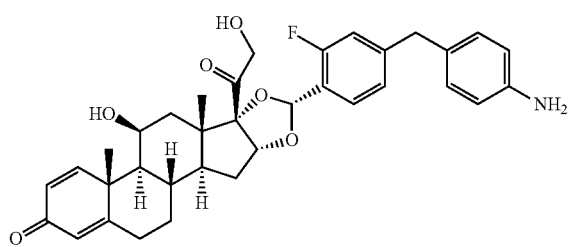

From Example 1, the residue was purified by reverse phase chromatography, eluting with 1:1 10 mM ammonium bicarbonate water +5% methanol:acetonitrile to give the title compound, isomer 2, peak 2 (225 mg, 9% yield). ES/MS m/z 588.4 (M+H). $^1$H NMR (500.11 MHz, d$_6$-DMSO) d 0.86 (s, 3H), 1.05 (dd, J=3.0, 11.1 Hz, 1H), 1.25-1.20 (m, 2H), 1.38 (s, 4H), 1.85-1.78 (m, 5H), 2.09-2.00 (m, 2H), 2.32-2.29 (m, 1H), 2.56-2.53 (m, 1H), 3.73 (s, 2H), 4.02-3.97 (m, 1H), 4.22-4.17 (m, 1H), 4.30-4.29 (m, 1H), 4.78 (d, J=3.1 Hz, 1H), 4.87 (s, 2H), 4.98 (t, J=6.0 Hz, 1H), 5.28 (d, J=6.8 Hz, 1H), 5.93 (s, 1H), 6.16 (dd, J=1.7, 10.1 Hz, 1H), 6.23 (s, 1H), 6.47 (d, J=8.2 Hz, 2H), 6.84 (d, J=8.2 Hz, 2H), 6.99-6.95 (m, 2H), 7.16 (t, J=7.7 Hz, 1H), 7.32-7.30 (m, 1H).

Example 3

(6aR,6bS,7S,8aS,8bS,10R,11aR,12aS,12bS)-10-(4-(4-Aminobenzyl)-2-fluorophenyl)-7-hydroxy-6a,8a-dimethyl-8b-(2-(((2R,3R,4S,5R,6R)-3,4,5-trihydroxy-6-(hydroxymethyl)tetrahydro-2H-pyran-2-yl)oxy)acetyl)-1,2,6a,6b,7,8,8a,8b,11a,12,12a,12b-dodecahydro-4H-naphtho[2',1':4,5]indeno[1,2-d][1,3]dioxol-4-one

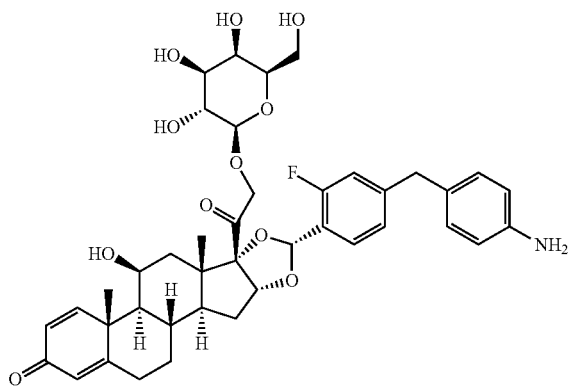

(2R,3S,4S,5R,6R)-2-(Acetoxymethyl)-6-(2-(((6aR,6bS,7S,8aS,8bS,10R,11aR,12aS,12bS)-10-(4-(4-aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)tetrahydro-2H-pyran-3,4,5-triyl triacetate (45 mg, 0.05 mmol, see Preparation 2), methanol (2 mL), and potassium carbonate (25 mg, 0.25 mmol) were added to a flask and stirred at rt for 1 hr. The crude solution was concentrated under reduced pressure to give a residue. The residue was purified by reverse phase chromatography, eluting with 3:7 10 mM ammonium bicarbonate water+5% methanol:acetonitrile to give the title compound (23 mg, 63% yield). ES/MS m/z 750.4 (M+H). $^1$H NMR (500.11 MHz, d$_6$-DMSO) δ 0.88 (s, 3H); 1.06-1.03 (m, 2H), 1.40 (s, 3H), 1.77-1.69 (m, 3H), 1.81 (d, J=1.8 Hz, 2H), 2.04-2.00 (m, 1H), 2.17-2.14 (m, 1H), 2.38-2.32 (m, 1H), 2.58-2.53 (m, 1H), 3.18 (d, J=5.4 Hz, 1H), 3.31-3.26 (m, 1H), 3.39-3.34 (m, 1H), 3.55-3.47 (m, 2H), 3.63 (t, J=4.1 Hz, 1H), 3.74 (s, 2H), 4.20 (d, J=7.6 Hz, 1H), 4.31-4.30 (m, 1H), 4.47-4.41 (m, 2H), 4.65 (t, J=5.5 Hz, 1H), 4.78-4.72 (m, 3H), 4.89 (s, 2H), 4.94 (dd, J=5.0, 9.9 Hz, 2H), 5.64 (s, 1H), 5.93 (s, 1H), 6.17 (dd, J=1.8, 10.1 Hz, 1H), 6.49-6.46 (m, 2H), 6.86 (d, J=8.3 Hz, 2H), 7.06-7.01 (m, 2H), 7.32 (d, J=10.0 Hz, 1H), 7.47 (t, J=7.7 Hz, 1H).

Example 4

(2S,3S,4S,5R,6R)-6-(2-(((6aR,6bS,7S,8aS,8bS,10R,11aR,12aS,12bS)-10-(4-(4-Aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)-3,4,5-trihydroxytetrahydro-2H-pyran-2-carboxylic acid

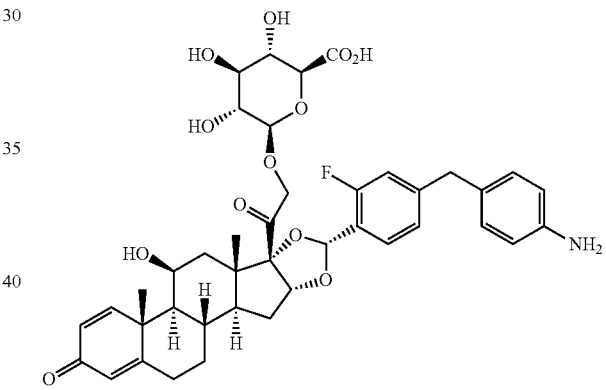

(2R,3R,4S,5S,6S)-2-(2-(((6aR,6bS,7S,8aS,8bS,10R,11aR,12aS,12bS)-10-(4-(4-Aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)-6-(methoxycarbonyl)tetrahydro-2H-pyran-3,4,5-triyl triacetate (44 mg, 0.05 mmol, see Preparation 3), methanol (2 mL), and potassium carbonate (25 mg, 0.25 mmol) were added together, and stirred at rt for 2.5 hrs. The crude solution was concentrated under reduced pressure to give a residue. The residue was purified by reverse phase chromatography, eluting with 1:1 10 mM ammonium bicarbonate water +5% methanol:acetonitrile to give the title compound (24 mg, 65% yield). ES/MS m/z 764.4 (M+H). 1H NMR (500.11 MHz, d$_6$-DMSO) d 0.84 (s, 3H), 1.07-0.98 (m, 2H), 1.41 (s, 3H), 1.76-1.66 (m, 4H), 2.16-2.11 (m, 2H), 2.45-2.44 (m, 1H), 2.60-2.55 (m, 1H), 3.05-3.04 (m, 1H), 3.20-3.18 (m, 2H), 3.74 (s, 2H), 4.40-4.30 (m, 2H), 4.58-4.52 (m, 1H), 4.82-4.78 (m, 1H), 4.95-4.92 (m, 2H), 5.13-5.11 (m, 2H), 5.64 (s, 1H), 5.92 (s, 1H), 6.16 (dd, J=1.3, 10.0 Hz, 1H), 6.48 (d, J=8.1 Hz, 2H), 6.86 (d, J=8.1 Hz, 2H), 7.11-7.09 (m, 2H), 7.36-7.32 (m, 1H), 7.51-7.45 (m, 1H).

Example 5

2-((6aR,6bS,7S,8aS,8bS,10R,11aR,12aS,12bS)-10-(4-(4-Aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl dihydrogen phosphate

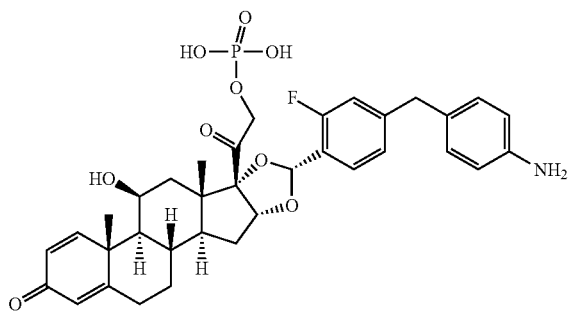

2-((6aR,6bS,7S,8aS,8bS,10R,11aR,12aS,12bS)-10-(4-(4-Aminobenzyl)-2-dioxol-8b-yl)-2-oxoethyl di-tert-butyl phosphate (165 mg, 0.19 mmol, see Preparation 7) was dissolved in dichloromethane (2 mL) and trifluoroacetic acid (1 mL) was added. The reaction was stirred at rt for 1 hr. The crude solution was neutralized with saturated aqueous sodium bicarbonate solution and extracted with ethyl acetate. The combined organic layers were dried over sodium sulfate, filtered, and concentrated under reduced pressure to give a residue. The residue was purified by reverse phase chromatography, eluting with 7:3 10 mM ammonium bicarbonate water:acetonitrile to give the title compound (34 mg, 26% yield). ES/MS m/z 668.2 (M+H). 1H NMR (500.11 MHz, $d_6$-DMSO) d 0.79-0.72 (m, 1H), 0.89 (s, 4H), 1.38 (s, 3H), 1.66-1.55 (m, 1H), 1.73-1.67 (m, 2H), 2.10-2.08 (m, 2H), 2.27-2.22 (m, 2H), 3.67 (s, 2H), 3.67 (brs, 4H), 4.19 (d, J=1.8 Hz, 1H), 4.78-4.69 (m, 2H), 4.94 (d, J=4.9 Hz, 1H), 5.58 (s, 1H), 5.88 (s, 1H), 6.11-6.08 (m, 1H), 6.46 (d, J=8.3 Hz, 2H), 6.87-6.80 (m, 4H), 7.38-7.28 (m, 5H).

Example 6

(6aR,6bS,7S,8aS,8bS,10R,11aR,12aS,12bS)-10-(4-(4-aminobenzyl)-2-fluorophenyl)-7-hydroxy-6a,8a-dimethyl-8b-(2-(((2R,3R,4S,5S,6R)-3,4,5-trihydroxy-6-(hydroxymethyl)tetrahydro-2H-pyran-2-yl)oxy)acetyl)-1,2,6a,6b,7,8,8a,8b,11a,12,12a,12b-dodecahydro-4H-naphtho[2',1':4,5]indeno[1,2-d][1,3]dioxol-4-one

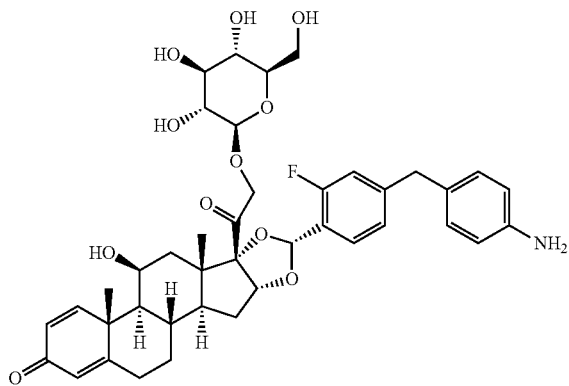

(2R,3R,4S,5R,6R)-2-(acetoxymethyl)-6-(2-((6aR,6bS,7S,8aS,8bS,10R,11aR,12aS,12bS)-10-(4-(4-aminobenzyl)-2-fluorophenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)tetrahydro-2H-pyran-3,4,5-triyl triacetate (120 mg, 0.13 mmol, see Preparation 8), methanol (2 mL), and potassium carbonate (65 mg, 0.66 mmol) were added to a round bottomed flask and stirred at rt for 1 h. The crude solution was loaded onto celite and was purified by reverse phase chromatography, eluting with 3:7 10 mM ammonium bicarbonate water +5% methanol:acetonitrile to give title compound (78 mg, 78% yield). MS m/z 750.4 (M+H). 1H NMR (500.11 MHz, $d_6$-DMSO) δ 7.48-7.45 (m, 1H), 7.34-7.30 (m, 1H), 7.07-7.01 (m, 2H), 6.86 (d, J=8.3 Hz, 2H), 6.48 (d, J=8.3 Hz, 2H), 6.25-6.16 (m, 1H), 5.95-5.93 (m, 1H), 5.66 (s, 1H), 5.11 (d, J=4.9 Hz, 1H), 4.98-4.88 (m, 5H), 4.79-4.74 (m, 2H), 4.62-4.59 (m, 1H), 4.50-4.46 (m, 1H), 4.38-4.29 (m, 1H), 4.25-4.23 (m, 1H), 3.74 (s, 2H), 3.71-3.67 (m, 1H), 3.50-3.48 (m, 1H), 3.17-3.13 (m, 4H), 2.38-2.34 (m, 1H), 2.16-2.14 (m, 2H), 1.84-1.75 (m, 5H), 1.40 (s, 3H), 1.07-1.05 (m, 2H), 0.89-0.88 (m, 3H).

hGR CoActivator Recruitment Assay

The activity of glucocorticoid compounds was measured using the LanthaScreen™ TR-Fret GR Coactivator Assay from Life Technologies (A15899). The compounds were acoustically transferred to an assay plate in a 3-fold 10-point serial dilution with a top concentration of 200 nM. Ten microliters of a 2× solution of GR-LBD was added to the compound plate and incubated for 10 min. Then ten microliters of a 2× solution of Fluoresein-SRC1-4 and Tb labelled anti-GST antibody were added to the plate. The plate was incubated in the dark for two hours and then read on an Envision™ plate reader, with excitation at 340 nm and emission at 520 nm (Fluorescein) and 490 nm (Terbium). The emission ratio of 520/490 was analyzed in Genedata®. To obtain percent activity, the data was compared to a negative control of DMSO and positive control of 4 uM dexamethasone.

Following the procedure as essentially described above, the compound of Example 1 provided a relative $IC_{50}$ of 2.07 nM and the compound of Example 2 provided a relative $IC_{50}$ of 13.1 nM.

What is claimed is:
1. A compound of the formula:

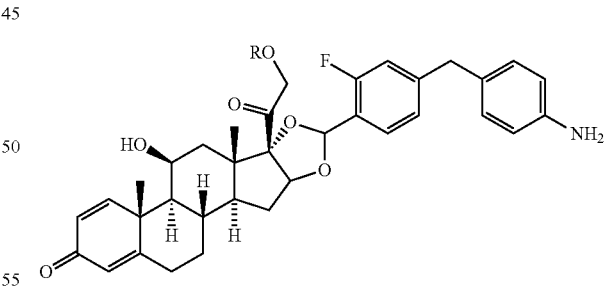

wherein R is hydrogen, —P(=O)(OH)$_2$,

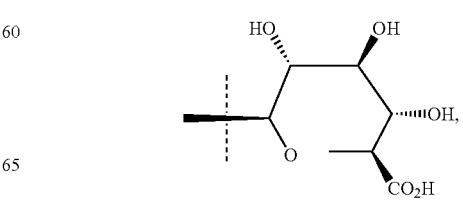

-continued

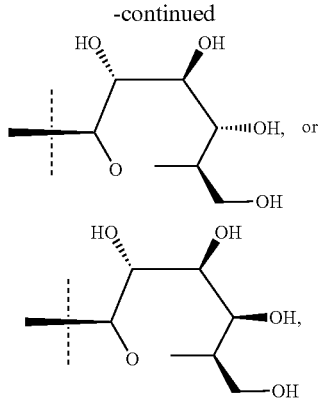

or a pharmaceutically acceptable salt thereof.

2. The compound of claim 1, wherein R is hydrogen, or a pharmaceutically acceptable salt thereof.

3. The compound of claim 1, wherein R is —P(=O)(OH)$_2$, or a pharmaceutically acceptable salt thereof.

4. The compound of claim 1, wherein R is:

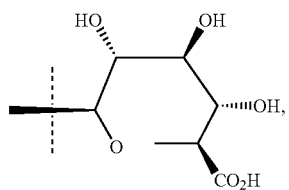

or a pharmaceutically acceptable salt thereof.

5. The compound of claim 1, wherein R is:

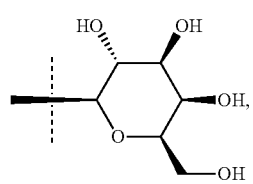

or a pharmaceutically acceptable salt thereof.

6. The compound of claim 1, wherein R is:

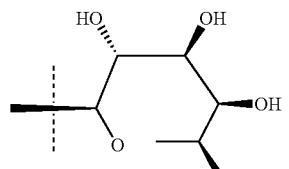

or a pharmaceutically acceptable salt thereof.

7. The compound according to claim 1, wherein the compound is:

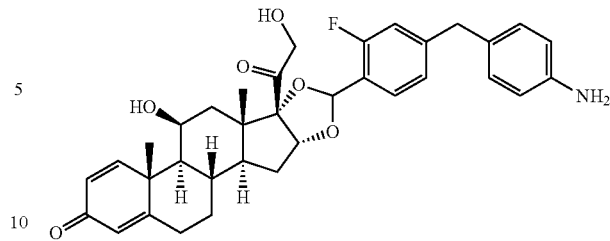

or a pharmaceutically acceptable salt thereof.

8. The compound according to claim 7, wherein the compound is:

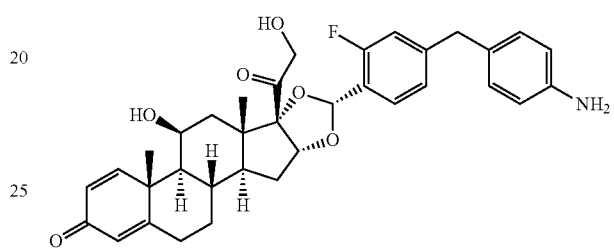

or a pharmaceutically acceptable salt thereof.

9. The compound according to claim 8 which is:

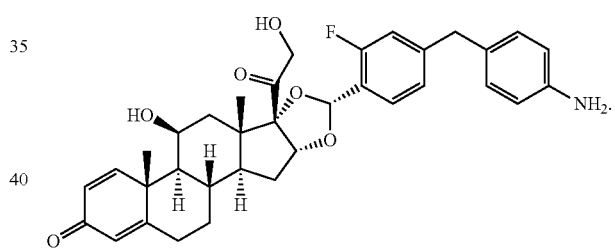

10. The compound according to claim 1 wherein the compound is:

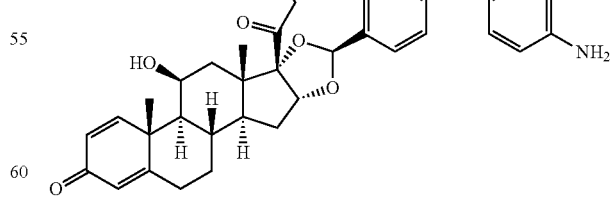

or a pharmaceutically acceptable salt thereof.

11. The compound according to claim 10, which is:

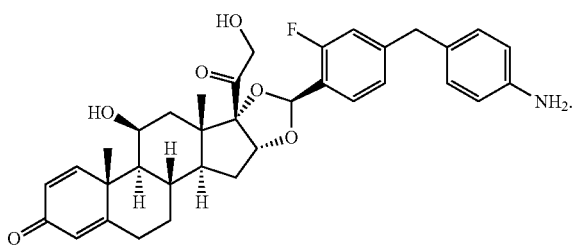

12. The compound according to claim 6, wherein the compound is:

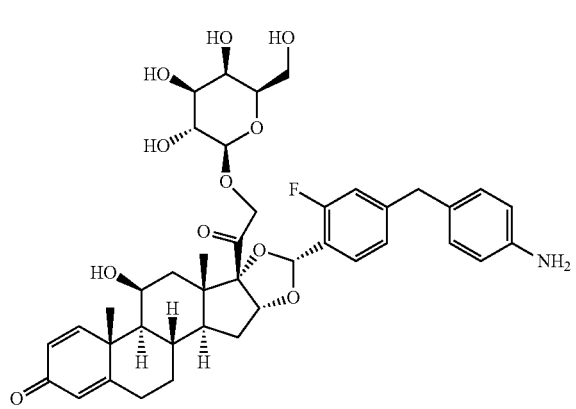

or a pharmaceutically acceptable salt thereof.

13. The compound according to claim 12, which is:

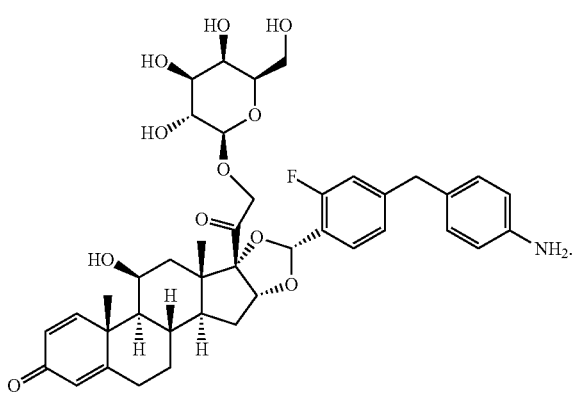

14. The compound according to claim 1, wherein the compound is:

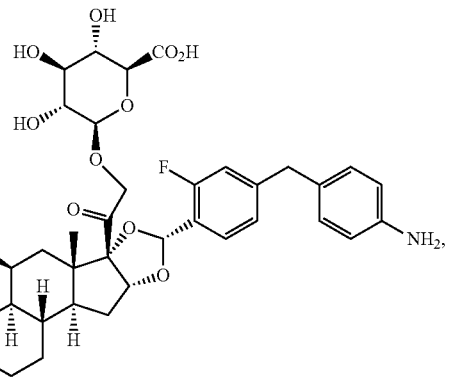

or a pharmaceutically acceptable salt thereof.

15. The compound according to claim 3, wherein the compound is:

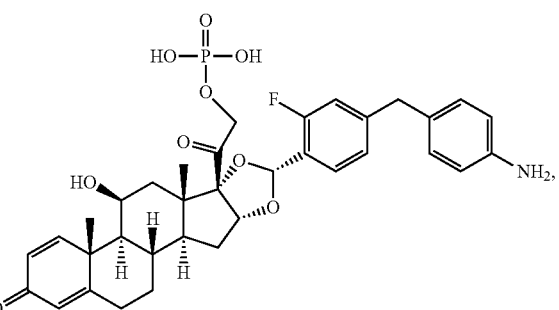

or a pharmaceutically acceptable salt thereof.

16. The compound according to claim 5, wherein the compound is:

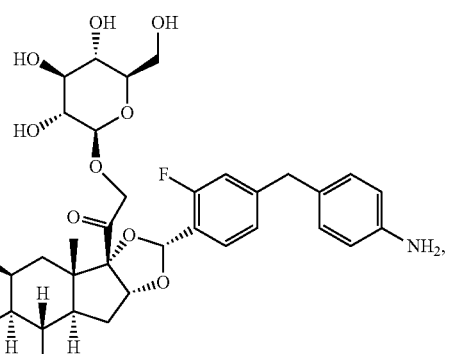

or a pharmaceutically acceptable salt thereof.

17. A method of treating atopic dermatitis in a patient, comprising administering to a patient in need of such treatment an effective amount of a compound according to claim 1, or a pharmaceutically acceptable salt thereof.

18. A method of treating systemic lupus erythematosus in a patient, comprising administering to a patient in need of such treatment an effective amount of a compound according to claim 1, or a pharmaceutically acceptable salt thereof.

19. A method of treating rheumatoid arthritis in a patient, comprising administering to a patient in need of such treatment an effective amount of a compound according to claim 1, or a pharmaceutically acceptable salt thereof.

20. A method of treating lupus nephritis in a patient, comprising administering to a patient in need of such treatment an effective amount of a compound according to claim 1, or a pharmaceutically acceptable salt thereof.

21. A method of treating inflammatory bowel disease in a patient, comprising administering to a patient in need of such treatment an effective amount of a compound according to claim 1, or a pharmaceutically acceptable salt thereof.

22. A pharmaceutical composition, comprising a compound or a pharmaceutically acceptable salt thereof, according to claim 1 with one or more pharmaceutically acceptable carriers, diluents, or excipients.

23. A process for preparing a pharmaceutical composition, comprising admixing a compound or a pharmaceutically acceptable salt thereof according to claim 1 with one or more pharmaceutically acceptable carriers, diluents, or excipients.

\* \* \* \* \*

UNITED STATES PATENT AND TRADEMARK OFFICE
CERTIFICATE OF CORRECTION

PATENT NO. : 12,227,538 B2  
APPLICATION NO. : 17/700910  
DATED : February 18, 2025  
INVENTOR(S) : Donmienne Doen Mun Leung, Jacqueline Mary Wurst and James Andrew Jamison Page 1 of 1

It is certified that error appears in the above-identified patent and that said Letters Patent is hereby corrected as shown below:

In the Claims

In Claim 5, delete " 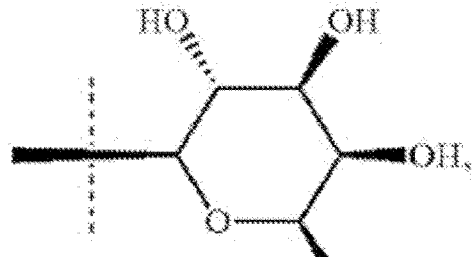 " and insert 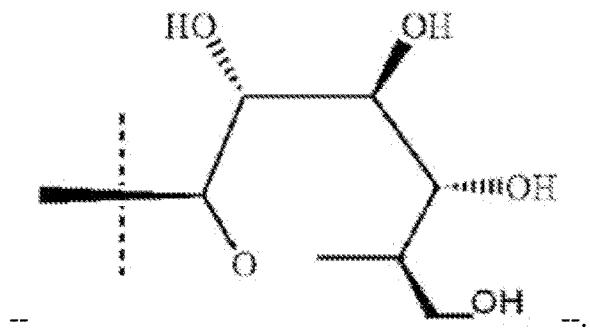 --.

Signed and Sealed this  
Sixteenth Day of September, 2025

Coke Morgan Stewart  
*Acting Director of the United States Patent and Trademark Office*